United States Patent
Holt et al.

(10) Patent No.: US 10,627,411 B2
(45) Date of Patent: Apr. 21, 2020

(54) T-CELL EPITOPE IDENTIFICATION

(71) Applicant: BRITISH COLUMBIA CANCER AGENCY, Vancouver (CA)

(72) Inventors: Robert Holt, Vancouver (CA); Govinda Sharma, Vancouver (CA)

(73) Assignee: British Columbia Cancer Agency Branch, Vancouver, British Columbia (CA)

( * ) Notice: Subject to any disclaimer, the term of this patent is extended or adjusted under 35 U.S.C. 154(b) by 132 days.

(21) Appl. No.: 15/128,923

(22) PCT Filed: Mar. 25, 2015

(86) PCT No.: PCT/CA2015/050230
§ 371 (c)(1),
(2) Date: Sep. 23, 2016

(87) PCT Pub. No.: WO2015/143558
PCT Pub. Date: Oct. 1, 2015

(65) Prior Publication Data
US 2018/0052176 A1 Feb. 22, 2018

Related U.S. Application Data

(60) Provisional application No. 61/971,355, filed on Mar. 27, 2014.

(51) Int. Cl.
| | | |
|---|---|---|
| *C12N 5/00* | (2006.01) |
| *C12N 5/02* | (2006.01) |
| *G01N 33/53* | (2006.01) |
| *G01N 33/68* | (2006.01) |
| *C12Q 1/6886* | (2018.01) |
| *C12N 15/10* | (2006.01) |
| *G01N 33/50* | (2006.01) |
| *G01N 33/569* | (2006.01) |

(52) U.S. Cl.
CPC ..... *G01N 33/6878* (2013.01); *C12N 15/1037* (2013.01); *C12N 15/1086* (2013.01); *C12Q 1/6886* (2013.01); *G01N 33/5091* (2013.01); *G01N 33/56972* (2013.01); *G01N 33/6845* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,989,505 A | 11/1999 | Storkus |
| 6,218,165 B1 | 4/2001 | Estell |
| 6,780,598 B1 | 8/2004 | Kokolus |
| 6,897,049 B1 | 5/2005 | Estell |
| 6,936,249 B1 | 8/2005 | Estell |
| 7,430,476 B2 | 9/2008 | Carr |
| 7,756,644 B2 | 7/2010 | Fridman |
| 7,803,566 B2 | 9/2010 | Terajima |
| 2002/0119121 A1* | 8/2002 | Vitiello ............. A61K 39/0011 424/85.2 |
| 2004/0132132 A1 | 7/2004 | Sahin |
| 2007/0184493 A1* | 8/2007 | Packard ................ A61K 38/07 435/7.2 |
| 2008/0220450 A1 | 9/2008 | Harding |
| 2013/0195900 A1 | 8/2013 | Dornmair |

FOREIGN PATENT DOCUMENTS

| | | |
|---|---|---|
| WO | WO2004/063963 A2 | 7/2004 |
| WO | WO2005/080991 A1 | 9/2005 |
| WO | WO2011/032722 A2 | 3/2011 |
| WO | WO2012/022975 A1 | 2/2012 |
| WO | WO 2018/227091 A1 | 12/2018 |

OTHER PUBLICATIONS

Choi et al., Apr. 16, 2013, PNAS< vol. 110: 6488-6493.*
Cassidy et al., 2014, Front. Immunol. vol. 5: 1-8.*
Chavez-Galan et al., 2009, vol. 6: 15-25.*
Backes et al, "GraBCas: a bioinformatics tool for score-based prediction of Caspase-and Granzyme B-cleavage sites in protein sequences," Nucleic Acids Research, 33:W208-W213 (2005).
Barrett et al, "Chimeric antigen receptor therapy for cancer," Annu. Rev. Med., 65: 333-347 (2014).
Boon et al, "Human tumor antigens recognized by T lymphocytes," J. Exp. Med., 183: 725-729 (1996).
Brentjens et al, "CD19-targeted T cells rapidly induce molecular remissions in adults with chemotherapy-refractory acute lymphoblastic leukemia," Science Translational Medicine, 5(177): 177ra38 (2013).
Bryson et al, "Prediction of immunogenicity of therapeutic proteins," Biodrugs, 24(1): 1-8 (2010).
Cantor et al, "Therapeutic enzyme deimmunization by combinatorial T-cell epitope removal using neutral drift," Proc. Natl. Acad. Sci., 108(4): 1272-1277 (2011).
Castle et at, "Exploiting the mutanome for tumor vaccination," Cancer Research, 72(5): 1-11 (2012).

(Continued)

Primary Examiner — Amy E Juedes
(74) Attorney, Agent, or Firm — Stephen C. Macevicz

(57) ABSTRACT

The present invention is a method for determining the identity of the epitopes recognized by T-cells. The method consists of expressing an encoded library of candidate epitope sequences in a recipient reporter cell capable of providing a detectable signal upon cytotoxic attack from a single cognate T-cell followed by contacting the reporter cells with T-cells of interest. The reporter cells with a single indicating cytotoxic attack from a T-cell are isolated and then analyzed by next-generation sequencing in order to identify the epitope sequences. Specifically disclosed is a method in which a library of candidate epitope-encoding nucleic acids are expressed in cells which feature a membrane-bound major histocompatibility complex (MHC) protein, said library produced by transfection of plasmids featuring both a nucleotide encoding the candidate epitope and a nucleotide encoding a FRET-based fluorescent protein cleaved by granzyme.

8 Claims, 8 Drawing Sheets

(56) References Cited

OTHER PUBLICATIONS

Ewen et al, "A quarter century of granzymes," Cell Death and Differentiation, 19: 28-35 (2012).
Felber et al, "Evaluation of the CFP-substrate-YFP system for protease studies: advantages and limitations," Biotechniques, 36(5); 878-885 (2004).
Gupta et al, "Development of highly sensitive Bicistronic vector based non-radioactive antigen-specific cytotoxicity assay," J. Immunol. Methods, 349: 28-37 (2009).
Halene et al, "Improved expression in hematopoietic and lymphoid cells in mice after transplantation of bone marrow transduced with a modified retroviral vector," Blood, 94(10): 3349-3357 (1999).
Hondowicz et al, "Discovery of T cell antigens by high-throughput screening of synthetic minigene libraries," Plos One, 7(1): e29949 (2012).
Kawakami et al, "Cloning of the gene coding for a shared human melanoma antigen recognized by autologous T cells infiltrating into tumor," Proc. Natl. Acad. Sci., 91(9): 3515-3519 (1994).
Keefe et al, "Perforin triggers a plasma membrane-repair response that facilitates CTL induction of apoptosis," Immunity, 23: 249-262 (2005).
Krensky et al, "Granulysin: a novel host defense molecule," Am. J. Transplantation, 5: 1789-1792 (2005).
Law et al, "The structural basis for membrane binding and pore formation by lymphocyte perforin" Nature, 468: 447-451 (2010).
Li et al, "Cancer genome sequencing and its implications for personalized cancer vaccines," Cancers, 3: 4191-4211 (2011).
Liechtenstein et al, "Lentiviral vectors for cancer immunotherapy and clinical applications," Cancers, 5: 815-837 (2013).
Lundegaard et al, "Predictions versus high-throughput experiments in T-cell epitope discovery: competition or synergy?" Expert Rev. Vaccines, 11(1): 43-54 (2012).
Maus et al, "Antibody-modified T cells: CARs take the front seat for hematologic malignancies," Blood, 123(17): 2625-2635 (2014).
Messitt et al, "A comparison of two methods for T cell epitope mapping: "cell free" in vitro versus immunoinformatics," Immunome Research, 7:2:6 (2011).
Metkar et al, "Perforin rapidly induces plasma membrane phospholipid flip-flop," PLosOne 6(9): e24286 (2011).
Molecular Probes, "CellEvent® caspase~3/7 green flow cytometry assay kit" Product description (2012).
Pastan et al, "Immunotoxin therapy of cancer," Nature Reviews Cancer, 6: 559-565 (2006).
Porter et al, "Chimeric antigen receptor-modified T cells in chronic lymphoid leukemia," New England Journal of Medicine, 365(8): 725-733 (2011).
Sharma et al, "T-cell epitope discovery technologies," Human Immunology, 75: 514-519 (2014).
Siewert et al, "Unbiased identification of target antigens of CD8+ T cells with combinatorial libraries coding for short peptides," Nature Medicine, 18(5): 824-828 and Supplemental material (2012).
Thiery et al, "Perforin pores in the endosomal membrane trigger the release of endocytosed granzyme B into the cytosol of target cells," Nature Immunology, 12(8): 770-777 (2011) including Supplemental materials.
Tong et al, "Methods and protocols for prediction of immunogenic epitopes," Briefings in Bioinformatics, 8(2): 96-108 (2006).
Trapani, "Granzymes: a family of lymphocyte granule serine proteases," Genome Biology, 2(12): reviews 3014.1-3014.7 (2001).
Trapani et al, "Functional significance of the perforin/granzyme cell death pathway," Nature Reviews Immunology, 2: 735-747 (2002).
Vonderheide et al, "Engineering T cells for cancer: our synthetic future," Immunological Reviews, 257: 7-13 (2014).
Woodsworth et al, "Sequence analysis of T-cell repertoires in health and disease," Genome Medicine, 5: 98 (2013).
Xu et al. "Detection of programmed cell death using fluorescence energy transfer," Nucleic Acids Research, 26(8): 2034-2035 (1998).
Brichard et al, "The tyrosinas gene codes for an antigen recognized by autologous cytolytic T lymphocytes on HLA-A2 melanomas," J. Exp. Med. 178: 489-495 (1993).
Joglekar et al, "T cell antigen discovery via signaling and antigen-presenting bi-functional receptors," Nature Methods, 16: 191-198 (2019).
Kawakami et al, "Identification of a human melanoma antigen recognized by tumor-infiltrating lymphocytes associated with in vivo tumor rejection," Proc. Natl. Acad. Sci., 91: 6458-6462 (1994).
Li et al, "T cell antigen discovery via trogocytosis," Nature Methods, 16: 183-190 (2019).
Linnemann et al, "High-throughput epitope discovety reveals frequent recognition of neo-antigens by CD4+ T cells in human melanoma," Nature Medicine, 21(1): 81-85 (2015) with online methods.
Lu et al. "Efficient identification of mutated cancer antigens recognized by T cells associated with durable tumor regressions," Clinical Cancer Research, 20(13): 3401-3410 (2014).
Robbins et al, "Mining exomic sequencing data to identify mutated antigens recognized by adoptively transferred tumor-reactive T cells," Nature Medicine, 19(6): 747-752 (2013).
van der Bruggen et al, "A gene encoding an antigen receignized by cytolytic T lymphocytes on a human melanoma," Science, 254(5038): 1643-1647 (1991).
Wick et al, "Surveillance of the tumor mutanome by T cells during progression from primary to recurrent ovarian cancer," Clinical Cancer Research, 20(5): 1125-1134 (2013).
Kula et al, "T-Scan: A genome-wide method for the systematic discovery of T cell epitopes," Cell, 178: 1016-1028 (2019).
Do et al, "GFP variants with alternative β-strands and application as a light-driven protease sensor: a tale of two tails," J. Am. Chem. Soc., 135(28): 10226-10229 (2013).
Pacini et al., "Reporter substrates for assessing the activity of the hepatitis C virus NS3-4A serine protease in living cells," Analytical Biochemistry, 331(1): 46-59 (2004).
To et al, "Rationally designed fluorogenic protease reporter visualizes spatiotemporal dynamics of apoptosis in vivo," Proc. Natl. Acad. Sci., 112(11): 3338-3343 (2015).
Wigdal et al "A novel bioluminescent protease assay using engineered firefly luciferase," Current Chemical Genomics, 2: 16-28 (2008).
Mahrus et al, "Selective chemical and functional probes of granzymes A and B reveal granzyme B is a major effector of natural killer cell-mediated lysis of target cells," Chemistry & Biology, 12: 567-577 (2005).
Nicholls et al, "Mechanism of a genetically encoded dark-to-bright reporter for caspase activity," J. Biol. Chem., 286(28): 24977-24986 (2011).
Rawlings et al, "MEROPS: the peptidase database," Nucleic Acids Research, 38: D227-D233 (2010).
Zhang et al, "Visualization of caspace-3-like activity in cells using a genetically encoded fluorescent biosensor activated by protein cleavage," Nature Communications, 4: 2157 (DOI: 10.1038/ncomms3157) (published Jul. 16, 3013).

* cited by examiner

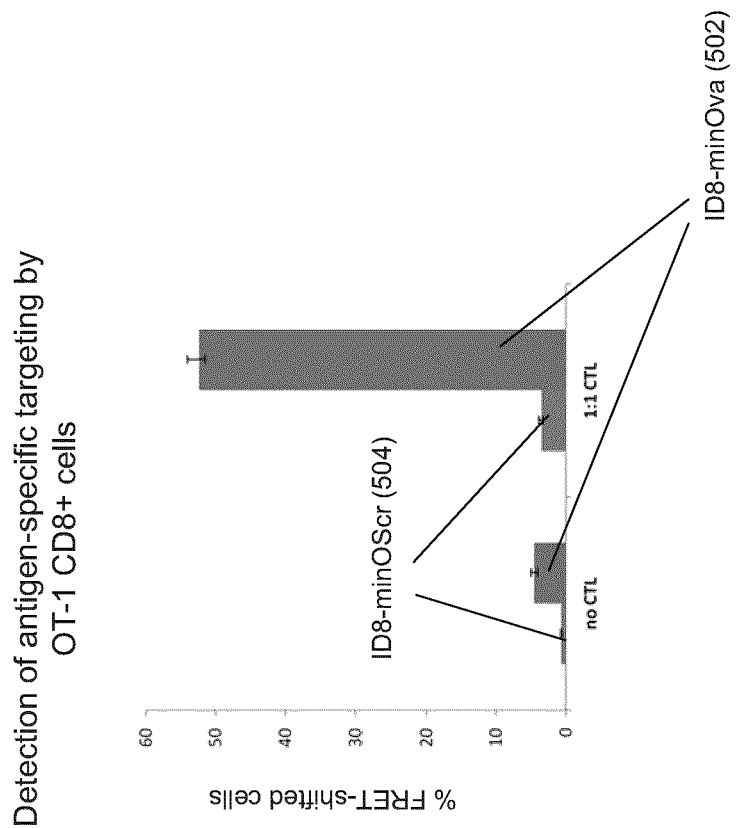

T-CELL EPITOPE IDENTIFICATION

BACKGROUND

The elucidation of CTL epitopes is crucial to the understanding of the molecular etiology of immune related disorders and the development of novel therapeutic strategies. Reliable identification of T-cell epitopes would, in particular, address an unmet need in the fields of cancer immunology, infectious disease, autoimmunity, and transplantation medicine. T-cell epitopes are short peptides displayed at the surface of antigen-presenting cells by the membrane-bound major histocompatibility complex (MHC) proteins, which are categorized as either class I or II. Class I molecules are expressed on the surface of nearly every cell of the body and present a sampling of short (8-14 residue) peptides derived from proteolytic turnover of proteins of both endogenous and exogenous origin. MHC class I found to be presenting epitopes recognized as 'non-self' are targets of direct attack from cytotoxic T-lymphocytes (CTLs).

The discovery of T-cell epitopes has proven to be a difficult endeavor given numerous characteristics of CTL antigen recognition including (a) extreme diversity of the T-cell repertoire generally ensures that clonotypes of interest are present in very low numbers, (b) T-cell epitope recognition is a low affinity interaction that must occur in the context of polygenic and highly polyallelic MHC molecules, (c) processing and presentation of both exogenous and endogenous peptides on MHC molecules makes for an enormous T-cell epitope space to be screened, and (d) substantial level of cross-reactivity is present in the T-cell repertoire, for example, it has been found that a single CTL is capable of recognizing on the order of $10^6$ different peptide-MHC (pMHC) antigens. Extensive research and development efforts in the field of T-cell epitope discovery have been ongoing over the previous three decades but to date no practical high throughput method is available to routinely identify T-cell epitopes, Sharma and Holt, Human Immunology, 75: 514-519 (2014).

In view of the above, the availability of a high throughput and convenient method to routinely identify epitopes of selected T cells would be highly advantageous to many fields in medicine and biology, including cancer immunotherapy, vaccine development, organ transplantation, autoimmune disease diagnosis and therapy, and the like.

SUMMARY OF THE INVENTION

The present invention is directed to methods and compositions for identifying and/or isolating T cell epitopes. Aspects of the present invention are exemplified in a number of implementations and applications, some of which are summarized below and throughout the specification.

In some embodiments the invention includes a method for determining epitopes recognized by cytotoxic lymphocytes comprising the steps of: (a) expressing a library of candidate epitope-encoding nucleic acids in reporter cells capable of presenting expressed peptides of such candidate epitope-encoding nucleic acids in the context of a membrane-bound major histocompatibility complex (MHC) protein and generating a signal upon recognition thereof by a cytotoxic lymphocyte and activation of effector functions of the cytotoxic T-cell; (b) contacting the reporter cells containing the expressed library of candidate epitope-encoding nucleic acids with a sample comprising cytotoxic lymphocytes; and (c) analyzing the candidate epitope-encoding nucleic acids of reporter cells that generate a signal indicating recognition by a cytotoxic lymphocyte of the sample to identify sequences of the epitope-encoding nucleic acids. In some embodiments, a step is included for isolating the reporter cells generating a signal indicating recognition by said cytotoxic lymphocyte. In particular, in such embodiments, the reporter cells may be genetically modified to express a FRET-based fluorescent protein signaling system that generates a fluorescent signal whenever enzymatically cleaved by an effector agent delivered to the reporter cell by a cytotoxic lymphocyte. In some embodiments, such effector agent is a granzyme.

In some embodiments, the invention includes a method for determining epitopes recognized by cytotoxic lymphocytes comprising the steps of: (a) expressing a library of candidate epitope-encoding nucleic acids or an enriched library of candidate epitope-encoding nucleic acids in reporter cells capable of presenting expressed peptides of such candidate epitope-encoding nucleic acids in the context of a membrane-bound major histocompatibility complex (MHC) protein and generating a signal upon recognition thereof by a cytotoxic lympohcyte and activation of effector functions of the cytotoxic lymphocyte; (b) contacting the reporter cells containing the expressed library of candidate epitope-encoding nucleic acids with a sample comprising cytotoxic lymphocytes; (c) isolating reporter cells generating a signal indicating recognition by a cytotoxic lymphocyte; (d) extracting candidate epitope-encoding nucleic acids from the isolated reporter cells and generating therefrom an enriched library of candidate epitope-encoding nucleic acids; (e) repeating steps (a)-(d) with the enriched library of candidate epitope-encoding nucleic acids until a frequency of reporter cells generating the signal indicating recognition by a cytotoxic lymphocyte is greater than or equal to a predetermined value; (f) analyzing the candidate epitope-encoding nucleic acids of reporter cells generating a signal to identify sequences of the epitope-encoding nucleic acids.

In other embodiments, the invention includes a method for testing the presence and/or level of cellular immunity in an individual to a predetermined antigen or class of antigens comprising the steps of: (a) providing reporter cells expressing a library of epitopes derived from the predetermined antigen or class of antigens, the reporter cells being MHC matched to the individual, the reported cells capable of generating a detectable signal in response to recognition by a cytotoxic T cell and activation of an effector response by cytotoxic T cell; (b) combining the reporter cells with a sample of cytotoxic T cells from the individual; and (c) determining the presence and/or level of cellular immunity of the individual to the predetermined antigen or class of antigens by a number or frequency of reporter cells generating a signal.

In another embodiment, the present invention provides a method for identifying epitopes suitable for use in vaccinations and other methods of stimulating the immune system to respond against infectious agents to effectively clear acute and latent infections.

In a still further embodiment, the present invention provides a method for identifying epitopes involved in autoimmune disorders and also organ transplant rejection and Graft Versus Host Disease, for the purpose of diagnosis and treatment of these disorders.

In another embodiment, the present invention provides a method for identifying epitopes suitable for use in vaccinations and other methods of inducing immune tolerance against commensal microorganisms or self-antigens.

In an alternative embodiment, the present invention provides a method for identifying the epitopes recognized by the public T-cell clonotypes associated with infectious agents or tumor neoantigens and to correlate these with effective immune responses.

In some embodiments, the method of the invention for determining the identity of the epitopes recognized by T-cells comprises the steps of: 1) expressing an encoded DNA, RNA or peptide library of candidate epitope sequences in a recipient reporter cell capable of providing a detectable signal upon cytotoxic attack from a single cognate T-cell; 2) contacting the reporter cells containing the library of candidate epitopes with T-cells of interest; 3) detecting and isolating the reporter cells with a signal indicating cytotoxic attack from a T-cell; and 4) analyzing the cells with a signal indicating cytotoxic T-cell attack to identify the epitope sequences. Methods of identifying epitope-encoding sequences include but are not limited to nucleic acid sequencing, peptide sequencing and hybridization, e.g. to microarrays of complementary hybridization probes.

In one embodiment, the candidate epitope sequences are expressed in recipient cells which provide a fluorescent signal upon cytotoxic attack from a single cognate T-cell. In one embodiment a Caspase-3/7 detection reagent is used to detect the induction of apoptosis. In an alternative embodiment, a genetically-encoded CFP-YFP fusion FRET pair separated by a granzyme B (GzmB)-cleavable linker is used. Further alternative methods known to researchers skilled in the art which provide a signal upon cytotoxic attack from a T-cell may be used.

In one embodiment the detection and isolation of the reporter cells emitting a signal indicating cytotoxic attack from a single cognate T-cell may be accomplished by flow cytometry or microfluidics methods.

In one aspect of the present invention, Tumour Infiltrating Lymphocytes (TILs) from a cancer patient may be added to the reporter cells in order to identify the epitopes that the Tumour Infiltrating Lymphocytes recognize. In further embodiments, cytotoxic T-cell antigens in particular CD8+ cytotoxic T lymphocytes from a cancer patient may be evaluated. In further alternative embodiments, T-cells from patients suffering from infections or immune disorders may be evaluated in order to identify the epitopes that said T-cells recognize.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTIONS OF THE DRAWINGS

Figure 2B:
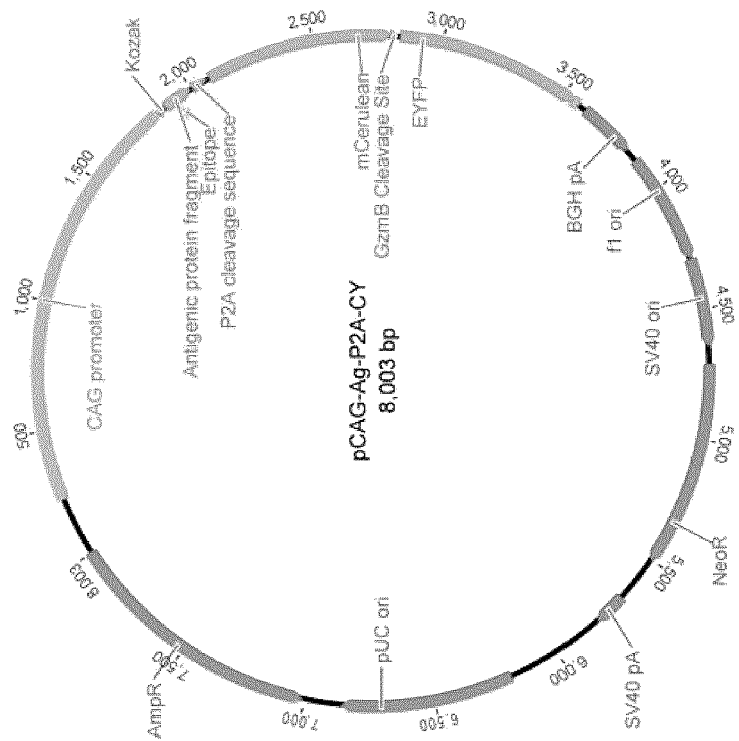
FIG. 2B illustrates diagrammatically a vector for transient co-transfection of reporter cells to provide control antigen or libraries of epitope-encoding nucleic acids.
Figure 2A:
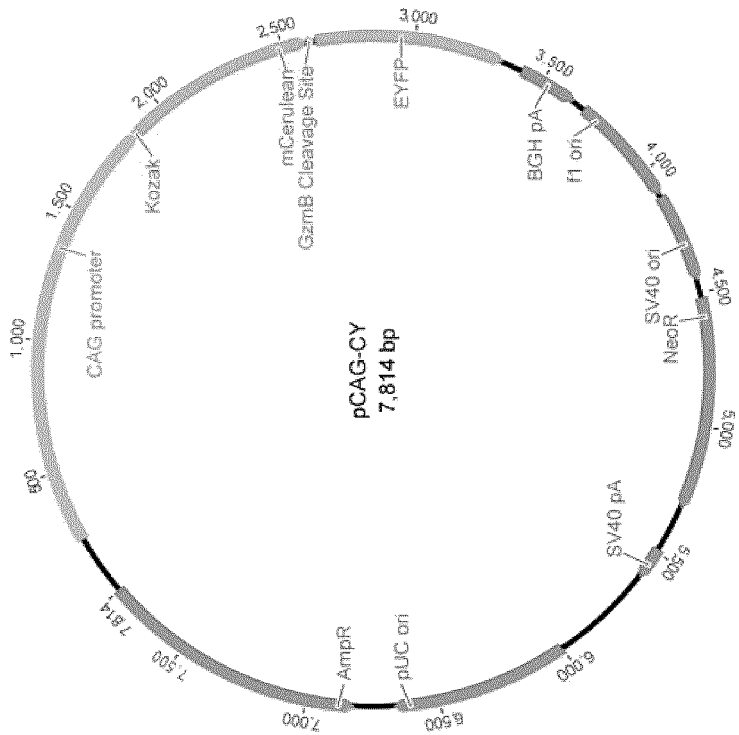
FIG. 2A illustrates diagrammatically a vector for transfecting the reporter cells to provide the reporter cells with a FRET signal generation product sensitive to granzyme B cleavage.
Figure 2C:
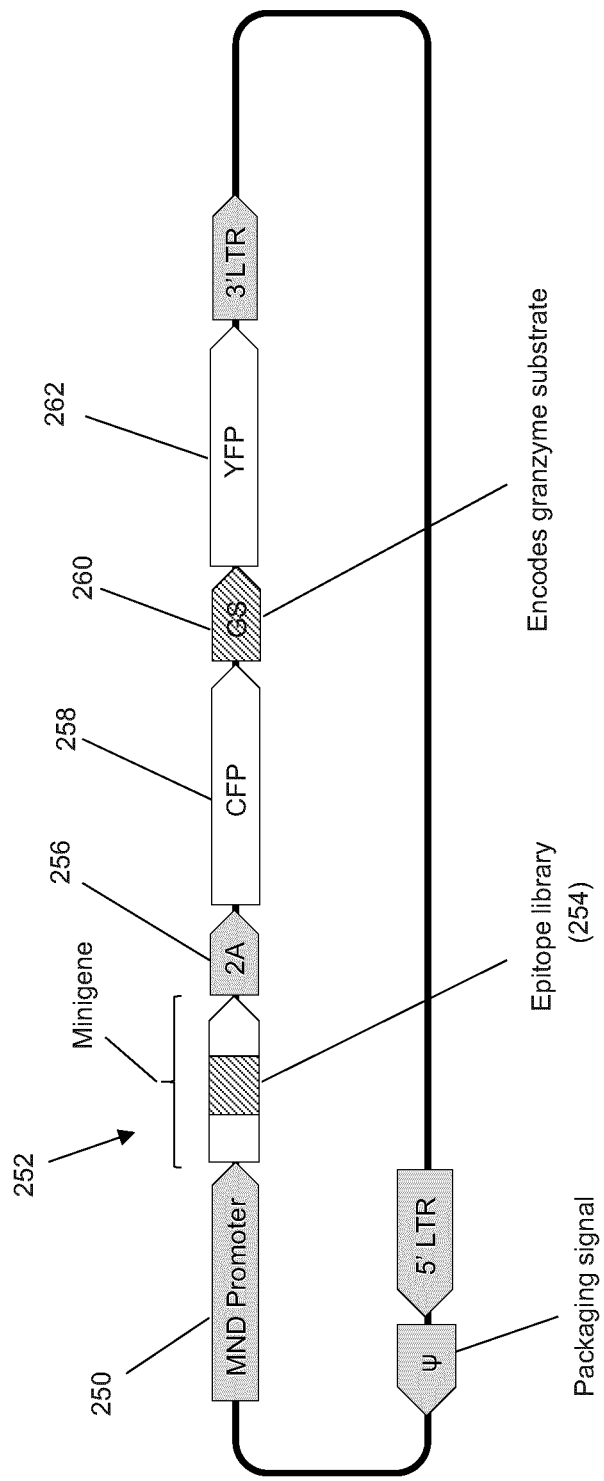

FIG. 2C diagrammatically illustrates a lentivirus vector containing a minigene capable of expressing candidate epitope-encoding nucleic acids or controls.

Figures 3A, 3B:
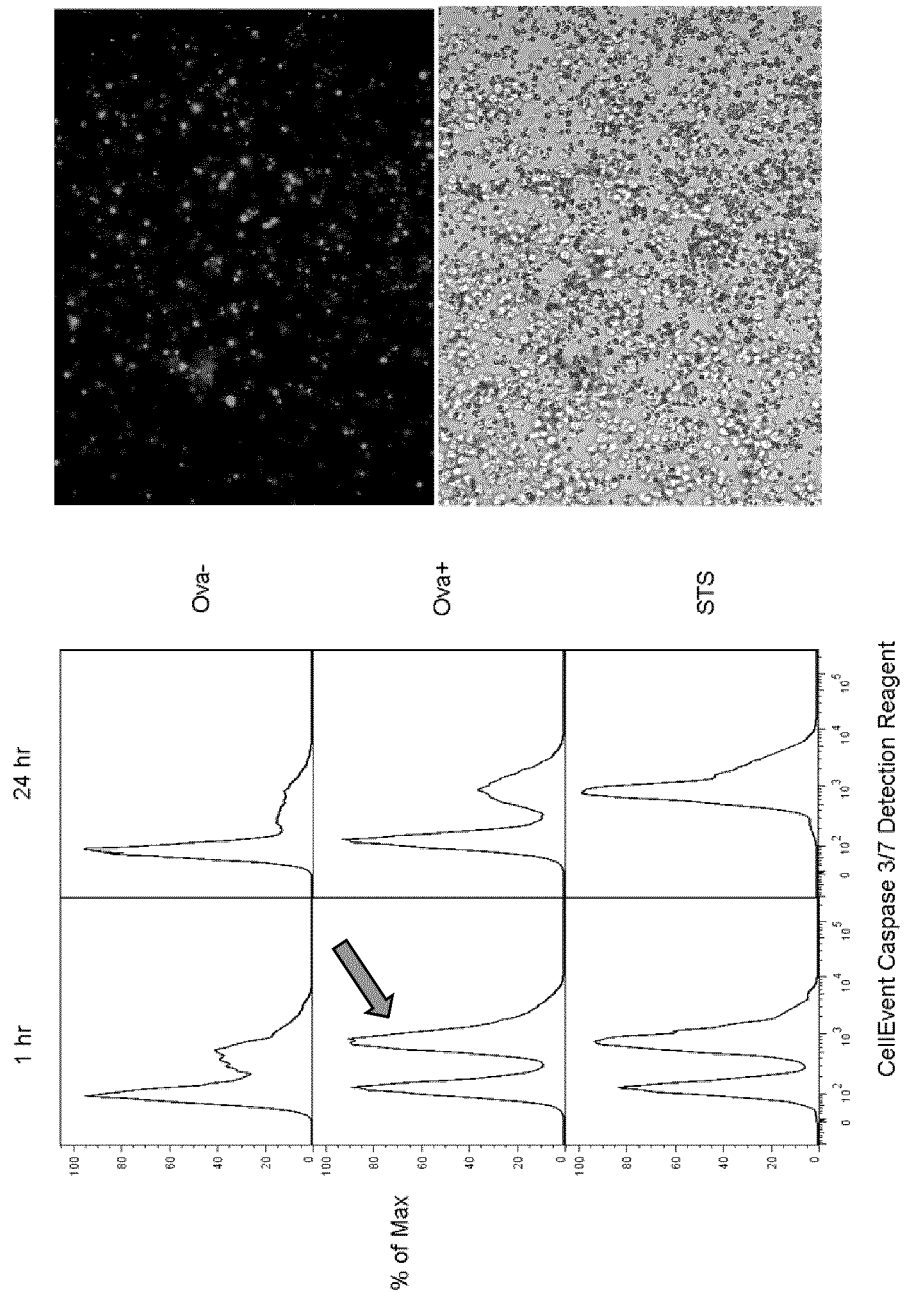

FIGS. 3A and 3B show data from optical signals generated by a model reporter cell of Example 1.

Figure 4:
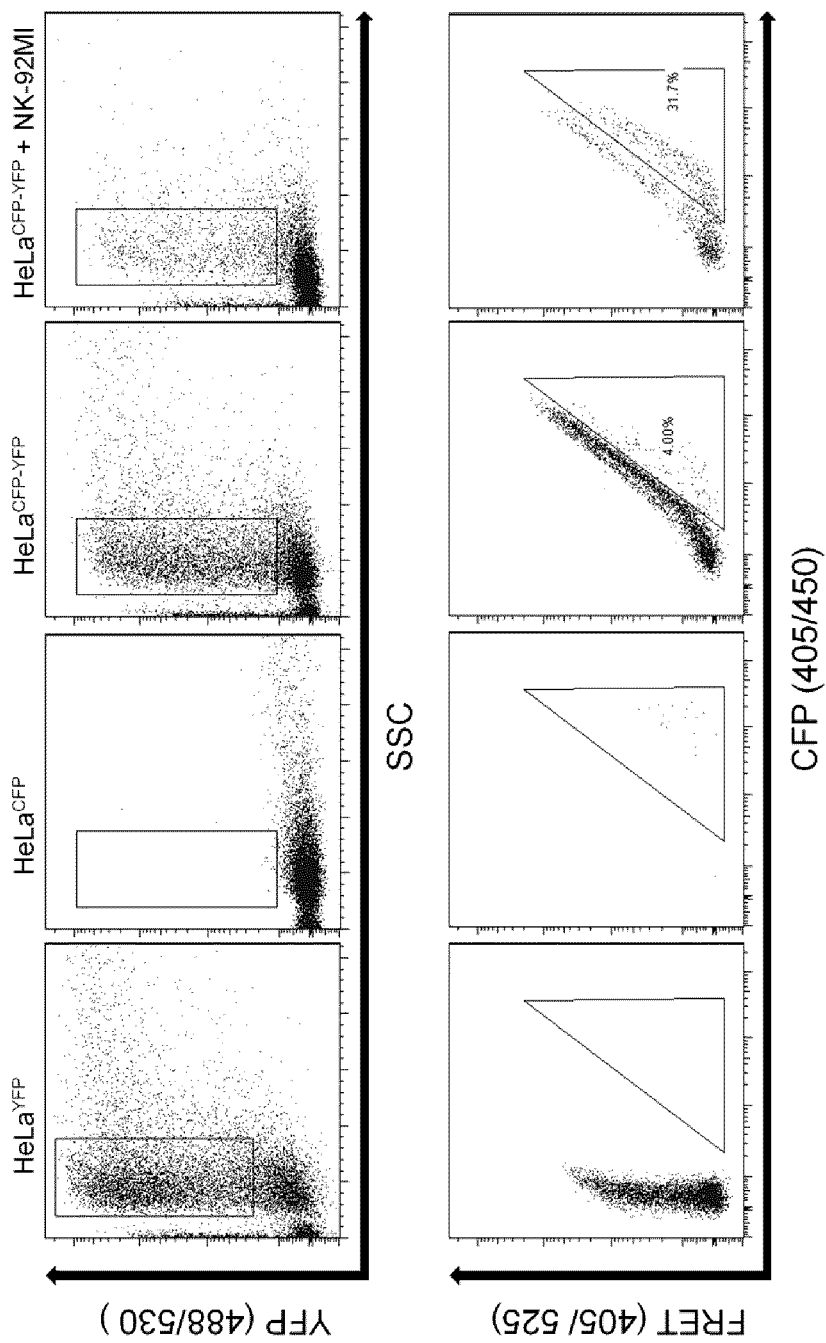

FIG. 4. Results of CTL assay employing GzmB-activatable CFP-YFP FRET pair. HeLa cells were transfected with either a YFP control plasmid, CFP control plasmid, or CFP-YFP plasmid from FIGS. 2A and 2B. NK-92MI cells were added to CFP-YFP containing HeLa for 4 h at a 5:1 E:T ratio. Viable transfectants were gated on by YFP signal and GzmB activity was monitored in FRET versus CFP plots.

Figure 5A:
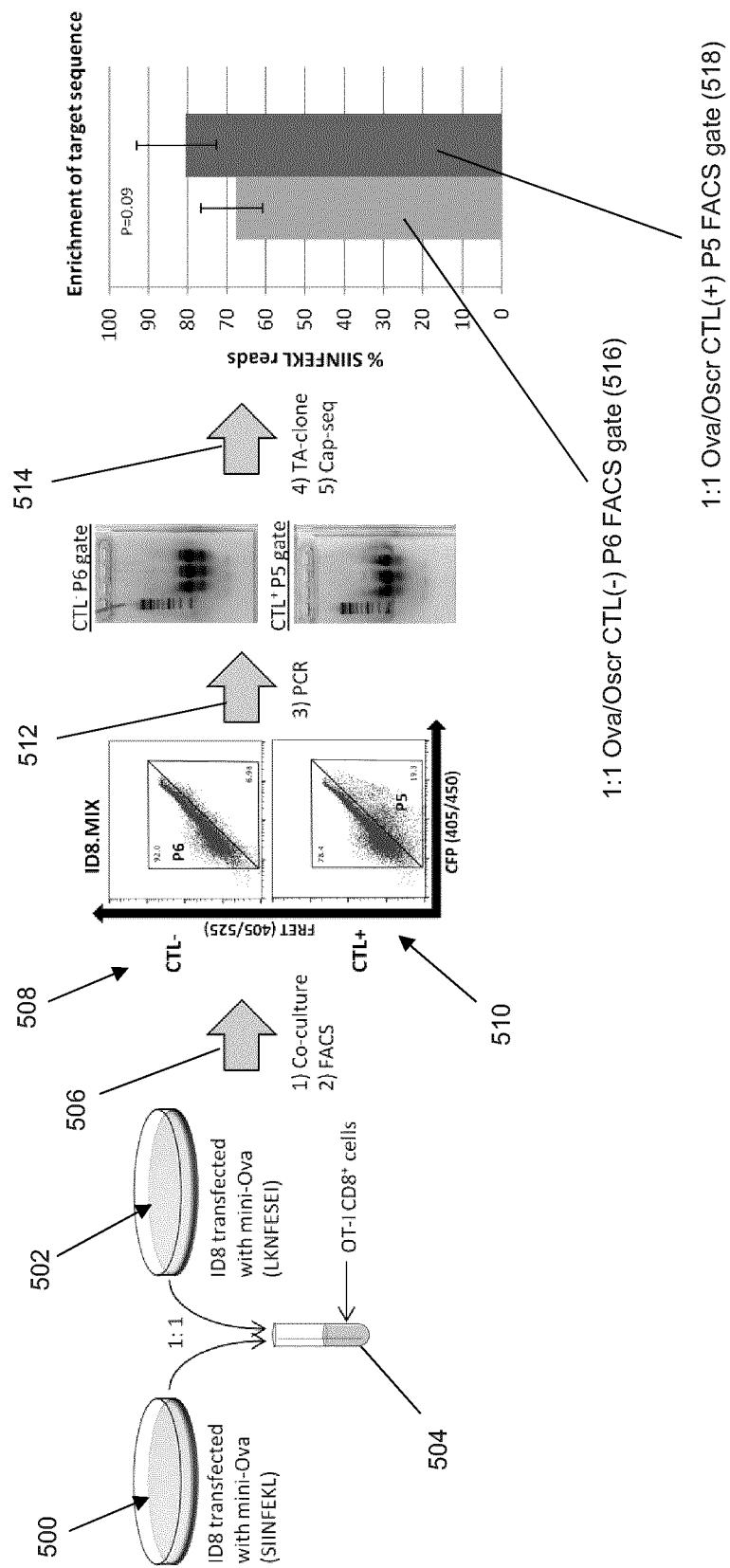

FIG. 5A Workflow and results of a preliminary minOva/minOScr sort-and-sequence experiment with transfected cells.

Figure 5B:
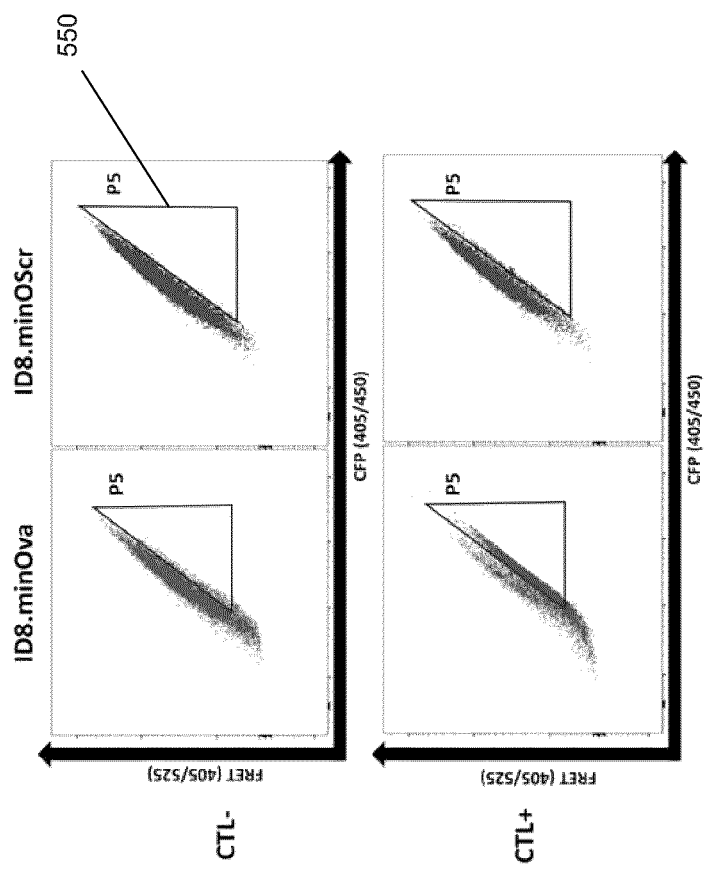

FIG. 5B shows plots of FRET signal (ex405/em525) versus CFP signal (ex405/em450) from the following experiment (Example 4): Target ID8 cells transduced with either OVA minigene (minOva) or OVA minigene containing scrambled epitope (minOScr) were cultured alone or with OT-1 CD8+ CTLs at a 1:1 ratio for 4 hrs.

FIG. 5C shows specific proportions of cells shifting into the P5 gate (550 FIG. 5B). The magnitude of this shift is small, but it is consistent with other FRET systems and is sufficient to allow highly stringent separation by FACS of antigen-presenting cells of interest.

DETAILED DESCRIPTION OF THE INVENTION

The practice of the present invention may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation and use of synthetic peptides, synthetic polynucleotides, monoclonal antibodies, nucleic acid cloning, amplifying, sequencing and analysis, and related techniques. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV); *PCR Primer: A Laboratory Manual; and Molecular Cloning: A Laboratory Manual* (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

The invention is directed to methods, compositions of matter and kits directed to the identification and/or isolation of T-cell epitopes of an individual. In one aspect, the invention provides reporter cells that are species and HLA matched to an individual (i.e. MHC matched), wherein such reporter cells express a library of epitopes for MHC-restricted presentation and wherein such reporter cells provide a detectable signal whenever a cytotoxic lymphocyte of the individual recognizes an MHC-epitope complex presented by such cells and is activated to produce an effector response or function. In some embodiments, a detectable signal permits reporter cells to be isolated and the nucleic acids encoding their epitopes analyzed for identification. In other embodiments, reporter cells that are recognized by an individual's cytotoxic lymphocytes are ruptured by apoptotic processes and release nucleic acids into a reaction mixture from which such cell-free epitope-encoding nucleic acids may be detected directly, for example, by amplification or by amplification and sequencing. In alternatives of the latter embodiments, additional steps may include separating the reaction mixture or culture supernatant from intact cells prior to amplification and sequencing. Guidance for isolating, amplifying and sequencing cell-free DNA of this latter embodiment is found in Oliphant et al, U.S. patent publication 2013/0143213, and like references, which are incorporated herein by reference.

In another aspect, such reporter cells are used in a method for determining epitopes recognized by T cells of an individual comprising the steps of: (a) contacting reporter cells expressing a library of epitopes with a sample of cytotoxic lymphocytes from the individual under conditions that permit the cytotoxic lymphocytes to have an effector response whenever their T cell receptors recognize a cognate epitope-MHC complex; (b) isolating reporter cells that have been recognized by cytotoxic lymphocytes and induced to generate a detectable signal; (c) analyzing the epitope-encoding nucleic acids of the isolated reporter cells to determine the identity of epitopes recognized by cytotoxic lymphocytes of the individual. The foregoing step of analyzing may be carried out by a variety of techniques, such as, hybridization to microarrays, DNA sequencing, polymerase chain reaction (PCR), quantitative PCR (qPCR), or like techniques. In some embodiments, the step of analyzing is carried out by sequencing the epitope-encoding nucleic acids. In other embodiments, the step of analyzing is carried out by amplifying the epitope-encoding nucleic acids from the isolated reporter cells, or a sample thereof, to form an amplicon, followed by DNA sequencing of member polynucleotides of the amplicon.

Figure 1A:
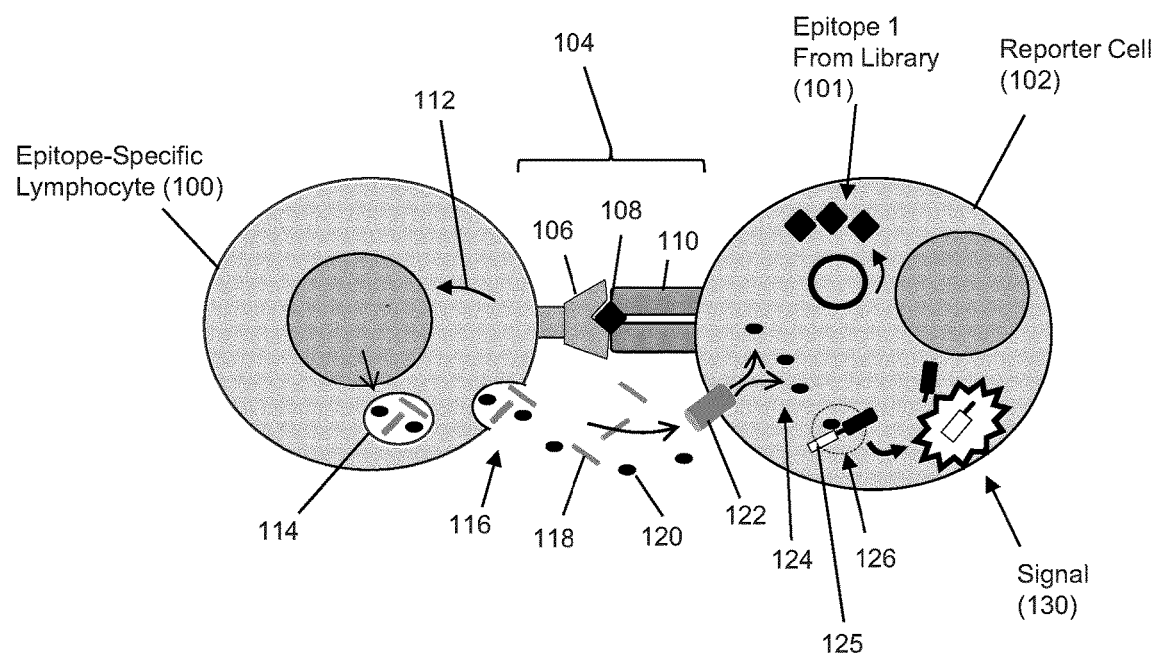
FIGS. 1A and 1B illustrate diagrammatically an embodiment of the invention for generating a fluorescent signal upon recognition of a reporter cell by a CTL and activation of the CTL (1A) and contrasts this with the absence of signal when a reporter cell is not recognized by a CTL.
Figure 1B:
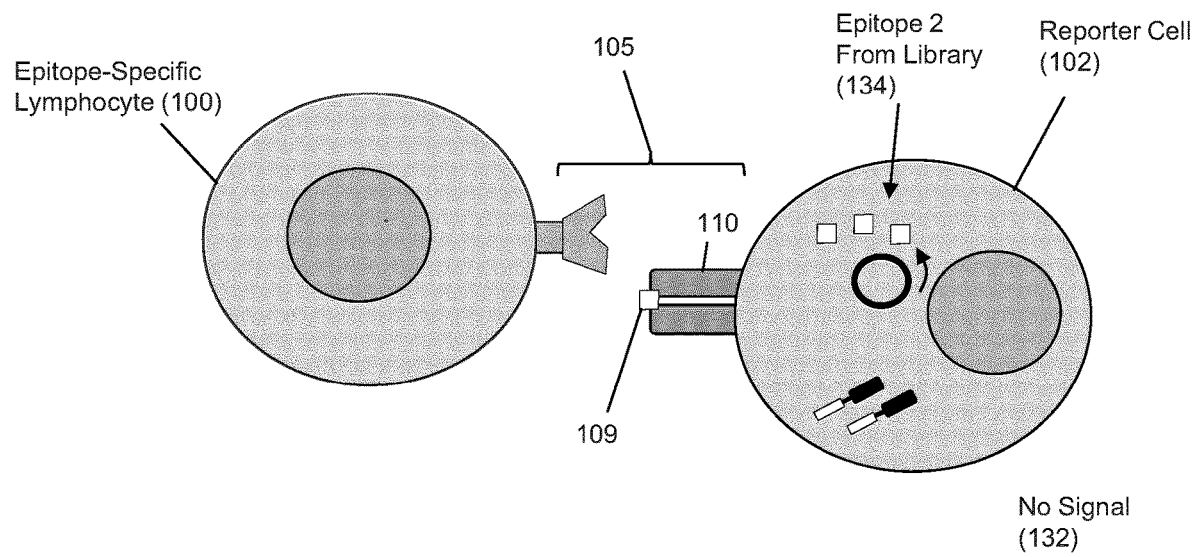

Features of the foregoing method are illustrated diagrammatically in FIGS. 1A and 1B. Reporter cells (102) are combined with cytotoxic lymphocytes (100), either individually using single cell techniques or in bulk by combining populations of each, under conditions that permit specific binding and recognition of an MHC-epitope complex by T cell receptors of the cytotoxic lymphocytes. In some embodiments, reporter cells and cytotoxic lymphocytes are combined in a reaction mixture under conventional tissue culture conditions for mammalian cell culture. Such reaction mixtures may include conventional mammalian cell culture media, such as DMEM, RPMI, or like commercially available compositions, with or without additional components such as indicators and buffering agents to control pH and ionic concentrations, physiological salts, growth factors, antibiotics, and like compounds. Reporter cells and cytotoxic lymphocytes may be incubated for a period of time, e.g. 30 min to 24 hours, or in other embodiments, 30 min to 6 hours, under such conditions to permit cell-cell contact and receptor recognition; that is, where T cell receptors of cytotoxic lymphocytes specifically recognize MHC-epitope complexes and generate an effector response that leads to the generation of a detectable signal in reporter cells. Returning to FIG. 1A, upon contact and specific recognition (104) of T cell receptor (106) and MHC-epitope complex (108 and 110), epitope-specific lymphocyte (100) is activated (111) to produce granules (114) that contain a variety of effector agents, including granzyme proteases (120) and perforins (118). As part of an effector response, granules of the activated epitope-specific lymphocyte (100) are transported to the cell surface and released (116) into the intercellular environment adjacent to reporter cell (102) by exocytosis. Perforins (118) assemble and form pores (122) through the cell membrane of reporter cell (102), after which granzymes and other effector agents enter (124) the cytosol of reporter cell (102). In some embodiments, a signal-generating structure (125) may comprise a quenched fluorescent protein that may be unquenched by granzyme cleavage (126) of a peptide link that releases a fluorescent moiety to generate signal (130).

In contrast, as illustrated in FIG. 1B, if no recognition and specific binding (105) occur between T cell receptors of epitope-specific lymphocyte (100) and MHC-epitope complex (110 and 109), for example, because epitope (109) is not recognized by the receptor, then no activation takes place, no effector agents get delivered to the cytosol of reporter cell (102), and no signal is generated (132). Thus, only reporter cells whose epitopes are recognized generate signals. Reporter cells may be isolated based on such signals and the nucleic acids encoding their epitope are determined. In some embodiments, recognized reporter cells generate optical signals and are isolated based on the presence, absence and/or level of such optical signal, e.g. by FACS. In some embodiments, recognized reporter cells generate a cell surface affinity molecule, e.g. as described by Pacini et al, Anal. Biochem., 331(1): 46-59 (2004), and like references, and may be isolated by affinity purification, panning, bead capture, or the like, using a complementary binding compound.

In one embodiment, high-throughput epitope screening involves the use of a reporter cell line genetically modified with an encoded library of candidate epitope-encoding nucleic acids that express products capable of fluorescing upon cytotoxic attack from a cytotoxic T-cell. Such genetic modification may be carried out by transient or stable transfection, transduction by conventional vectors, such as, retroviruses, lentiviruses, adenoviruses, adeno-associated viruses (AAVs), and the like, as well as by genetic engineering tools, such as, the CRISPR/Cas9 system, meganucleases, zinc finger nucleases, transcription activator-like effector nucleases (TALENs), and the like. Fluorescent cells can then be separated from the population at-large by fluorescence-activated cell sorting (FACS) and analyzed by next-generation sequencing (NGS). Schemes illustrating two implementations of this embodiment are shown in FIGS. 1A and 1B. Exemplary vectors for transfecting the reporter cells lines are illustrated in FIGS. 2A and 2B.

In accordance with the invention, identification of nucleic acids encoding reactive epitopes from sequence data may require application of well-known bioinformatics methods (e.g., Kent, Genome Res. 12 (4): 656-664 (2002)) for comparing sequence read data with database sequences of an individual's genome sequence or with other available databases of genomic sequences, transcriptome sequences, cancer genome sequences, or the like.

Iterative Determination of T Cell Epitopes

In some embodiments, a population of reporter cells expressing a library of epitopes may be exposed repeatedly to cytotoxic lymphocytes in successive cycles of steps that enrich the epitope-encoding library for signal-inducing epitopes after each cycle. In some such embodiments, successive cycles may include the steps of contacting reporter cells to a sample comprising cytotoxic lymphocytes of an individual, selecting or isolating responding reporter cells; expanding the selected or isolated reporter cells. These cycles may be repeated a predetermined number of times, e.g. 2-5 times, after which epitope-encoding nucleic acids are identified, for example, by amplification and sequencing, or the like. Alternatively, cycles may include an identifying step and the number of such cycles may be repeated until the number of epitope-encoding nucleic acids identified falls below a predetermined number, e.g. 20, and/or the frequencies of a predetermined number of epitope-encoding nucleic acids identified rises above a predetermined frequency.

In some embodiments, the above method for determining epitopes recognized by cytotoxic lymphocytes may be carried out by the following steps: (a) expressing a library of candidate epitope-encoding nucleic acids or an enriched library of candidate epitope-encoding nucleic acids in reporter cells capable of presenting expressed peptides of such candidate epitope-encoding nucleic acids in the context of a membrane-bound major histocompatibility complex (MHC) protein and generating a signal upon recognition thereof by a cytotoxic lymphocyte and activation of effector functions of the cytotoxic lymphocyte; (b) contacting the reporter cells containing the expressed library of candidate epitope-encoding nucleic acids with a sample comprising cytotoxic lymphocytes; (c) isolating reporter cells generating a signal indicating recognition by a cytotoxic lymphocyte; (d) extracting candidate epitope-encoding nucleic acids from the isolated reporter cells and generating therefrom an enriched library of candidate epitope-encoding nucleic acids; (e) repeating steps (a)-(d) with the enriched library of candidate epitope-encoding nucleic acids until a frequency of reporter cells generating the signal indicating recognition by a cytotoxic lymphocyte for each reporter cell is greater than or equal to a predetermined value; (f) analyzing the candidate epitope-encoding nucleic acids of reporter cells to identify sequences of the epitope-encoding nucleic acids. Exemplary frequencies of step (e) include at least 5 percent, at least 10 percent, at least 25 percent, or at least 50 percent. An enriched library of epitope-encoding nucleic acids may be constructed by amplifying the extracted candidate epitope-encoding nucleic acids (e.g. of step (d)), inserting them into a vector, stably transfecting or transforming autologous cells of the individual to produce a population of reporter cells expressing such enriched library.

Reporter Cells

In one aspect, a reporter cell of the invention has (1) the capability of presenting an epitope from a predetermined library of epitopes on its surface in the context of an MHC class I molecule so that a T cell recognizing it is activated to generate an effector response and (2) the capability of generating a detectable signal in response to effector agents from the T cell entering the cytosol of the reporter cell. In regard to (2), a detectable signal may be generated by direct action of an effector agent, e.g. granzyme B cleavage to release a quenched fluorescent moiety, or by indirect action of an effector agent, e.g. a caspase-activatable fluorescent reagent, such as CellEvent.

In some embodiments, reporter cells may be a primary or immortalized antigen presenting cell (APC) line that is MHC class I positive, and preferably, species matched and MHC matched with the individual whose T cell epitopes are being identified. Thus, in some embodiments, reporter cells may be derived from any autologous MHC class I positive cells of an individual. Such cells may be immortalized by conventional techniques, e.g. by viral transformation. In one embodiment, reporter cells may be autologous B cells, e.g. from the peripheral blood of the individual whose T cell epitopes are being identified, that have been transformed into B cell lymphoblastoid cells by viral transformation, for example, by EBV.

Alternatively, in some embodiments, if the sequence of the class I MHC molecule is known for an individual whose T cell epitopes are to be identified, then a reporter cell may be a non-autologous cell or cell line and may be transfected or transduced with a transgene encoding the individual's MHC class I molecule for expression on its surface, for example, as taught by Dornmair et al, U.S. patent publication 2013/0195900, which is incorporated herein by reference. In some embodiments, non-autologous cells or cells of a cell line may be transfected or transduced with a library comprising vectors that are all capable of expression the same patient-matched MHC class I molecule but different epitopes.

Epitopes from a predetermined library are introduced into reporter cells by transfection and/or transduction using conventional techniques. In some embodiments, reporter cells are transduced using a viral vector, such as a lentivirus, which results in a stable viral integration into the reporter cell genome. Transduction is carried out under conditions that result in on average no more than one viral integration event per target reporter cell. Transduction techniques include, but are not limited to, lipofection, electroporation, and the like.

As noted above, one function of a reporter cell is to generate a detectable signal whenever its displayed epitope is recognized by a T cell and the T cell generates an effector response. In some embodiments, a detectable signal is generated by a signal generating product expressed by one or more transgenes in the reporter cell. Such transgene may be inserted into the reporter cell by conventional transfection or transformation techniques. In some embodiments, the activity of protease effector agents, such as granzyme B, is employed directly or indirectly (e.g. via activation of a caspase protease) to activate signaling agents. In some embodiments, optical signals are generated by a FRET-based signaling system or a leuco-dye-based system wherein a cleavage event or other chemical modification converts a non-signaling reporter to one that generated an optical signal, e.g., Muthyala, Editor, "Chemistry and Applications of Leuco Dyes," (Plenum Press, New York, 1997). A wide variety of FRET-based and protein and organic leuco-dye signaling systems are available for use in the invention, including such systems that are genetically encoded, for example, fluorescent proteins, and that are delivered to reporter cells as membrane permeable reagents, for example, the CellEvent® reagent available from Invitrogen (Carlsbad, Calif.), the GranToxiLux® reagent available from Oncolmmunin, Inc. (Gaithersburg, Md.), and the like. FRET-based fluorescent protein signaling systems are commercially available and well-known in the art. Guidance for their application is described in the following exemplary references, which are incorporated by reference: Shimozono et al, Methods Cell Biol., 85: 381-393 (2008)(describing FRET-based signaling systems comprising cyan fluorescent protein (CFP) and yellow fluorescent protein (YFP)); Xu et al, Nucleic Acids Research, 26(8): 2034-2035 (1998)(describing FRET-based signaling systems comprising green fluorescent protein (GFP) and blue fluorescent protein (BFP)); Felber et al, Biotechniques, 36(5): 878-885 (2004); and the like. In some embodiments, a genetic construct (which may be part of a vector encoding epitopes) expresses a fusion protein which is a FRET-based signaling system having the form: FP1-p-FP2, where FP1 is an acceptor moiety, FP2 is a donor moiety, and p is a peptide linkage that contains a recognitions site for a protease. FP1 and FP2 are selected so that when held in proximity to one another by p, FP1 quenches fluorescent emissions by FP2, and whenever peptide linkage, p, is cleaved, FP1 and FP2 are release from one another so that FP2 emits a fluorescent signal freely. Vectors expressing such FRET-based signaling systems (or agents) may be constructed using conventional molecular biology techniques, as exemplified in the above-cited references and the examples below. Conventional techniques for protein expression in mammalian cells may be used in implementing variations of the invention, e.g. as disclosed by Hartley (Editor), "Protein expression in mammalian cells," Methods in Molecular Biology, vol. 801 (Humana Press, 2012).

Exemplary constructs for introducing signaling agents or systems into reporter cells are shown in FIGS. 2A and 2B. FIG. 2A shows vector pCAG-CY which may be used for validation of encodable signaling agents, in the case illustrated, a granzyme B-activatable FRET gene, and for stable reporter cell line development. FIG. 2B shows a plasmid containing a bicistronic antigen-reporter gene separated by a P2A self-cleaving sequence. This construct may be used for transient co-transfection of a control or test antigen or antigen libraries and a FRET reporter gene.

FIG. 2C illustrates diagrammatically one embodiment of a lentivirus construct for inserting both epitope-encoding nucleic acids and a FRET-based signaling system sensitive to granzyme B cleavage. The vector is based on the lentivirus vector disclosed by Halene et al. Blood. 94, 3349-57 (1999). Briefly, downstream of MND promoter (250) is inserted minigene (252) containing epitope-encoding nucleic acid (254) and flanking nucleic acids that may include primer binding sequences to facilitate identification after isolation, a P2A self-cleaving site (256) that permits discrete translation of epitope peptides and signaling proteins, gene (258) encoding a cyan fluorescent protein (CFP), nucleic acid (260) encoding a peptide linker cleavable by granzyme B, gene (262) encoding yellow fluorescent protein (YFP), as well as other lentivirus elements.

A variety of conventional techniques may be used to analyze epitope-encoding nucleic acids from reporter cells that have been induced to generate a signal indicating recognition and activation of a cognate T cell. In some embodiments, such reporter cells are first isolated then, in turn, the epitope-encoding nucleic acids are isolated from such cells. For example, in some embodiments epitopes are expressed from plasmids so that the encoding nucleic acids may be isolated using conventional miniprep techniques, for example, using commercially available kits, e.g. Qiagen (Valencia, Calif.), after which encoding sequences may be identified by such steps as PCR amplification, DNA sequencing or hybridization to complementary sequences. In other embodiments, where epitopes are expressed from integrated vectors, epitope-encoding nucleic acids from isolated reporter cells may be amplified from the reporter cell genome by PCR, followed by isolation and analysis of the resulting amplicon, for example, by DNA sequencing. In the latter embodiments, epitope-encoding nucleic acids may be flanked by primer binding sites to facilitate such analysis.

Exemplary human cell lines from which reporter cells may be constructed include, but are not limited to, HeLa, HEK293 and K562 cells, e.g. available commercially or from public repositories, such as the American Type Culture Collection (ATCC).

Epitope-Encoding Nucleic Acid Libraries

A wide variety of libraries of epitope-encoding nucleic acids may be used in the invention, which differ in size and structure of member sequences. Generally libraries will encode peptides that are capable of being processed by the MHC presentation and transport mechanisms of the reporter cells. In some embodiments, libraries comprise nucleic acids capable of encoding peptides at least eight amino acids in length; in other embodiments, libraries comprise nucleic acids capable of encoding peptides at least ten amino acids in length; in other embodiments, libraries comprise nucleic acids capable of encoding peptides at least 14 amino acids in length; in other embodiments, libraries comprise nucleic acids capable of encoding peptides at least 20 amino acids in length. Techniques for construction libraries encoding peptides and polypeptides is well-known in the art of therapeutic antibody development, where libraries are provided that comprise sequences of codons of various compositions. In some embodiments, where an epitope-encoding library is derived from a protein, members of such library may comprise nucleic acids encoding overlapping peptide segments of the protein. The lengths and degree of overlap of such peptides is a design choice for implementing the invention. In some embodiments, an epitope-encoding library includes a nucleic acids encoding every peptide segment of a collection of segments that covers the predetermined protein. In a further embodiment, such collection includes a series of segments of the same length each shifted by one amino acid along the length of the protein.

In some embodiments, the above codon substitutions are generated by synthesizing coding segments with degenerate codons, e.g. inserting one or more "NNN" codons. The coding segments are then ligated into a vector, such as a replicative form of a phage, to form a library. Many different degenerate codons may be used with the present invention, such as the exemplary condons shown in Table I.

TABLE I

Exemplary Degenerate Codons

| Codon* | Description | Stop Codons | Number |
|---|---|---|---|
| NNN | All 20 amino acids | TAA, TAG, TGA | 64 |
| NNK or NNS | All 20 amino acids | TAG | 32 |
| NNC | 15 amino acids | none | 16 |
| NWW | Charged, hydrophobic | TAA | 16 |
| RVK | Charged, hydrophobic | none | 12 |
| DVT | Hydrophilic | none | 9 |
| NVT | Charged, hydrophilic | none | 12 |
| NNT | Mixed | none | 16 |
| VVC | Hydrophilic | none | 9 |
| NTT | Hydrophobic | none | 4 |
| RST | Small side chains | none | 4 |
| TDK | Hydrophobic | TAG | 6 |

*Symbols follow the IUB code: N = G/A/T/C, K = G/T, S = G/C, W = A/T, R = A/G, V = G/A/C, and D = G/A/T.

In some embodiments, the size of epitope-encoding libraries used in the invention varies from about 1000 members to about $1 \times 10^5$ members; in another aspect, the size of libraries used in the invention varies from about 1000 members to about $5 \times 10^4$ members; and in further embodiments, the size of libraries used in the invention varies from about 2000 members to about $2.5 \times 10^4$ members. In still other embodiments, epitope-encoding libraries comprise at least 1000 member sequences; in still other embodiments, epitope-encoding libraries comprise at least $10^4$ members; in still other embodiments, epitope-encoding libraries comprise up to $10^4$ member sequences; in still other embodiments, epitope-encoding libraries comprise up to $10^5$ member sequences; in still other embodiments, epitope-encoding libraries comprise up to $10^6$ member sequences; in still other embodiments, epitope-encoding libraries comprise up to $10^7$ member sequences.

In some embodiments, epitope-encoding libraries for use with the invention may comprise random nucleotide sequences of a predetermined length, e.g. at least 24 nucleotides or greater in length. In other embodiments, epitope-encoding libraries for use with the invention may comprise sequences of randomly selected codons of a predetermined length, e.g. comprising a length of at least eight codons or more. In other embodiments, epitope-encoding libraries for use with the invention may comprise sequences of randomly selected codons of a predetermined length, e.g. comprising a length of at least 14 codons or more. In other embodiments, epitope-encoding libraries for use with the invention may comprise sequences of randomly selected codons of a predetermined length, e.g. comprising a length of at least 20 codons or more.

In other embodiments, epitope-encoding libraries depend on the tissue, lesion, sample, exome or genome of an individual from whom T cell epitopes are being identified. Epitope-encoding libraries may be derived from genomic DNA (gDNA), exomic DNA or cDNA. More particularly, epitope-encoding libraries may be derived from gDNA or cDNA from tumor tissue, microbially infected tissue, autoimmune lesions, graft tissue pre or post-transplant (to identify alloantigens), or gDNA from a microbiome sample, gDNA from a microbial (i.e. viral, bacterial, fungal) isolate. That is, peptides encoded by an epitope-encoding library may be derived from or represent actual coding sequences of the foregoing sources. Such libraries may comprise nucleic acids that cover, or include representatives, of all sequences in the foregoing sources or subsets of coding sequences in the foregoing sources. Such libraries based on actual coding sequences (i.e. sequences of codons) may be constructed as taught by Larman et al, Nature Biotechnology, 29(6): 535-541 (2011). Briefly, such methods comprising the steps of massively parallel synthesis on a microarray of epitope-encoding regions sandwiched between primer binding sites; cleaving or releasing synthesized sequences from the microarray; optionally amplifying the sequences; and cloning such sequences into a vector carrying the library. One of ordinary skill in the art would understand that such nucleic acid sequences would be inserted into an expression vector in an "in-frame" configuration with respect to promoter (and/or other) vector elements so that the amino acid sequences of peptides expressed correspond to those of the peptides found in the foregoing sources.

In some embodiments, epitope-encoding libraries are prepared from cDNA or gDNA from an individual whose T cell epitopes are being identified. In particular, when such individual is a cancer patient, such cDNA, gDNA, exome sequences, or the like, may be obtained, or extracted from, a cancerous tissue of the individual. In some embodiments, epitope-encoding libraries may be derived from sequences of cDNAs determined by cancer antigen-discovery techniques, such as, for example, SEREX (disclosed in Pfreundschuh, U.S. Pat. No. 5,698,396, which is incorporate herein by reference), and like techniques.

In still other embodiments, selection of epitope-encoding nucleic acids for a library may be guided by in silico T cell epitope prediction methods, including, but not limited to, those disclosed in the following references: Carr et al, U.S. Pat. No. 7,430,476; Chirino et al, International patent publication WO2004/063963; Parker et al, BMC Bioinformatics, 11: 180 (2010); Desai et al, Methods Mol. Biol., 1184: 333-364 (2014); Bhasin et al, Vaccine, 22(22-23): 195-204 (2004); Nielsen et al, Protein Science, 12(5): 1007-1017 (2003); Patronov et al, Open Biol 3: 120139 (2013); Lundegaard et al, Expert Rev. Vaccines, 11(1): 43-54 (2012); and the like. Briefly, candidate epitope-encoding nucleic acid sequences may be selected from all or parts (e.g. overlapping segments) of nucleic acids, e.g. genes or exons, encoding one or more proteins of an individual. In some embodiments, such protein-encoding nucleic acids may be obtained by sequencing all or part of an individual's genome. In other embodiments, such protein-encoding nucleic acids may be obtained from known cancer genes, including their common mutant forms.

Cytotoxic T-Cells

Cytotoxic T cells for use in methods of the invention may be obtained from virtually any source containing T cells, including, but not limited to, peripheral blood (e.g. as a peripheral blood mononuclear cell (PBMC) preparation), dissociated organs or tissue, including tumors, synovial fluid (e.g. from arthritic joints), ascites fluid or pleural effusion form cancer patients, cerebral spinal fluid, and the like. Sources of particular interest include tissues affected by diseases, such as cancers, autoimmune diseases, viral infections, and the like. In some embodiments, cytotoxic T cells used in methods of the invention are provided as a clonal population or a near clonal population. Such populations may be produced using conventional techniques, for example, sorting by FACS into individual wells of a microtitre plate, cloning by limited dilution, and the like, followed by growth and replication. In vitro expansion of the desired T lymphocytes can be carried out in accordance with known techniques (including but not limited to those described in U.S. Pat. No. 6,040,177 to Riddell et al.), or variations thereof that will be apparent to those skilled in the art.

Cytotoxic T cells from tissues affected by cancer, such as tissue-infiltrating T lymphocytes (TILs), are of special interest, and may be obtained as described in Dudley et al, J. Immunotherapy, 26(4): 332-342 (2003); Dudley et al, Semin. Oncol., 34(6): 524-531 (2007); and like references. Exemplary procedures for obtaining TIL include the following:

Excising normal and tumor tissues. Tumor specimens are excised aseptically, and tissue is processed under "good laboratory practice" conditions. All resected specimens are sampled for pathologic confirmation of the diagnosis of metastatic melanoma. "Feeder" lymphocytes as needed are obtained by apheresis of normal donors. All donors are required to undergo testing for infection with common blood-borne pathogens and viruses including RPR, HIV, LCMV, and HVC. Apheresis specimens from normal donors are purified on Ficoll-Hypaque step gradients (LSM Lymphocyte Separation Medium, ICN Biochemicals Inc., Aurora, Ohio) and cryopreserved. Human AB serum may be purchased from several commercial sources (Valley Biomedical, Winchester Va.; Gemini Bioproducts, Woodland, Calif.) after screening for optimal performance to promote the growth of lymphocyte clones.

Expansion of TIL microcultures. A tumor specimen is dissected free of surrounding normal tissue and necrotic areas. Small chunks of tumor (usually 8-16) measuring about 1 to 2 mm in each dimension are cut with a sharp scalpel from different areas around the tumor specimen. A single tumor fragment is placed in each well of a 24-well tissue culture plate with 2 mL of complete medium (CM) plus 6000 IU per mL of rhIL-2 (Chiron Corp., Emeryville, Calif.). CM consisted of RPMI 1640, 25 mmol/L HEPES pH 7.2, 100 U/mL penicillin, 100 µg/mL streptomycin, 2 mmol/L-glutamine, and $5.5 \times 10^{-5}$ mol/L β-mercaptoethanol, supplemented with 10% human serum. The plates are placed in a humidified 37° C. incubator with 5% CO2 and cultured until lymphocyte growth is evident. Each fragment is inspected about every other day using a low-power inverted microscope to monitor the extrusion and proliferation of lymphocytes. Whether or not lymphocyte growth is visible, half of the medium is replaced in all wells no later than 1 week after culture initiation. Typically, about 1 to 2 weeks after culture initiation, a dense lymphocytic carpet covers a portion of the plate surrounding each fragment. When any well becomes almost confluent, the contents are mixed vigorously, split into two daughter wells and filled to 2 mL per well with CM plus 6000 IU/mL IL-2. Subsequently, the cultures are split to maintain a cell density of $0.8$-$1.6 \times 10^6$ cells/mL, or half of the media was replaced at least twice weekly.

TIL cultures from single cell digests. Briefly, each solid tumor specimen is carefully dissected free of surrounding normal tissue and necrotic areas. The tumor is sliced with a sharp scalpel into small pieces (approximately 2 mm on each side). The tumor fragments are immersed in a mixture of collagenase, hyaluronidase, and DNAse in serum-free RPMI 1640, and incubated overnight with gentle agitation. The single-cell slurry is passed through sterile wire mesh to remove undigested tissue chunks. The digested single-cell suspensions are washed twice in HBSS, viable cells are purified on a single step Ficoll gradient, and cells are resuspended for plating. Multiple wells of a 24-well plate are seeded with $1 \times 10^6$ viable cells in 2 mL CM with 6000 IU/mL IL-2. The plates are placed in a humidified 37° C. incubator with 5% CO2. Whether or not lymphocyte growth is visible, half of the medium was replaced in all wells no later than 1 week after culture initiation. When any well became nearly confluent, the contents are mixed vigorously, split into two daughter wells, and filled to 2 mL per well with CM plus 6000 IU/mL IL-2. Subsequently, half the media is replaced at least twice weekly, or the cultures are split to maintain a cell density of 0.8 to $1.6 \times 10^6$ cells/mL. Some of the TIL from digests are derived from multiple original wells that were regularly mixed and eventually pooled for assessment of activity. Other TIL from digests are derived from individual wells of a 24-well plate. For these cultures, all progeny cells from any individual well are treated as an independent TIL culture and are maintained separately from the descendants of any other original well. In this way, multiple cultures may be obtained from the same initial single-cell suspension.

TIL cultures from disaggregation. In some embodiments, TILs are derived by a method of physical disaggregation of melanoma fragments using a device, such as a Medimachine (Becton Dickenson) with 50 μm "medicon" chambers, which are mini sterile and disposable homogenizers. Fragments of tumor about 2 mm per side may be prepared by dissection of biopsy specimens free from normal and necrotic tissue. Several fragments at a time may be physically disaggregated by a 30-second Medimachine treatment, which disaggregated the tumor chunks using mechanical shear provided by a rotating disk that forced the tumor chunks across a small grater inside the medicon. The resulting slurry of single cells and small cell aggregates is washed once, and resuspended in CM. The cell suspension is layered onto a two-step gradient with a lower step of 100% Ficoll, and a middle step of 75% Ficoll and 25% CM. After 20 minutes' centrifugation at 2000 rpm (about 1100 g), the interfaces are collected. The lower interface containing the lymphocyte-enriched fraction is processed separately from the upper interface containing the tumor-enriched cells. Each fraction is washed twice. The lower, TIL-enriched fraction is plated in 24-well plates, and individual TIL cultures are generated exactly as for the single-cell suspensions derived by enzymatic degradation.

Assaying TIL activity. TIL activity and specificity may be determined by analysis of cytokine secretion. TIL and control T-cell lines are washed twice prior to co-culture assay to remove IL-2. TIL cells ($1 \times 10^5$) are plated per well of a 96-well flat-bottom plate with $1 \times 10^5$ stimulator cells. TILs are generally stimulated. When available, TILs may be stimulated with an autologous tumor cell line or a thawed aliquot of cryopreserved single-cell tumor digests ("fresh tumor"). For some TILs, the TAP-deficient T2 cell line may be pulsed with tumor antigen peptides (for example, for melanoma: MART-1:27-35 (referred to as MART) or gp100: 209-217 (referred to as g209)). After overnight c-culture, supernatants are harvested and IFN-γ secretion is quantified by ELISA (e.g. Pierce/Endogen, Woburn, Mass.).

Nucleic Acid Sequencing Techniques

A variety of DNA sequence analyzers are available commercially to determine the nucleotide sequences epitope-encoding nucleic acids recovered from reporter cells in accordance with the invention. Commercial suppliers include, but are not limited to, 454 Life Sciences, Life Technologies Corp., Illumina, Inc., Pacific Biosciences, and the like. The use of particular types DNA sequence analyzers is a matter of design choice, where a particular analyzer type may have performance characteristics (e.g. long read lengths, high number of reads, short run time, cost, etc.) that are particularly suitable for the experimental circumstances. DNA sequence analyzers and their underlying chemistries have been reviewed in the following references, which are incorporated by reference for their guidance in selecting DNA sequence analyzers: Bentley et al, Nature, 456: 53-59 (2008); Margulies et al, Nature, 437: 376-380 (2005); Metzker, Nature Reviews Genetics, 11: 31-46 (2010); Fuller et al, Nature Biotechnology, 27: 1013-1023 (2009); Zhang et al, J. Genet. Genomics, 38(3): 95-109 (2011); and the like. Generally, epitope-encoding nucleic acids are extracted from reporter cells using conventional techniques and prepared for sequence analysis in accordance with manufacturer's instructions.

Assessing Cellular Immunity to Specific Antigens

In some embodiments, methods of the invention may be employed to test an individual's cellular immunity against an antigen or a class of antigens. One such method for testing the presence and/or level of cellular immunity in an individual to a predetermined antigen or class of antigens comprising the steps of: (a) providing reporter cells expressing a library of epitopes derived from the predetermined antigen or class of antigen, the reporter cells being MHC matched to the individual; (b) exposing the reporter cells to a sample of T cells of the individual; (c) determining the presence and/or level of cellular immunity of the individual to the predetermined antigen or class of antigen by a number or frequency of reporter cells generating a signal. Antigens or antigen classes from which an epitope library is constructed may vary widely. For example, antigens may include coat or surface proteins of infectious agents, such as infectious bacteria or viruses, allergens, and the like. Classes of antigen may include antigenic proteins from collections of infectious diseases, such as multiple strains of influenza, or the like. Classes of antigen may also include tumor proteins or tumor markers of an individual, for example, identified by SEREX, or like techniques.

In some embodiments, a method for testing the presence and/or level of cellular immunity in an individual to an infectious agent comprises the steps of: (a) providing reporter cells expressing a library of epitopes derived from the infectious agent, the reporter cells being MHC matched to the individual; (b) exposing the reporter cells to a sample of T cells of the individual; (c) determining the presence and/or level of cellular immunity of the individual to the infectious agent by a number or frequency of reporter cells generating a signal. In some embodiments, infectious agents may include viruses, bacteria, fungus, or protozoan agents.

Further Applications

Applications of the invention include identifying T cell-antigen interaction in any circumstance in health or disease where such interaction is an in situ immune response, including, but not limited to, the circumstances of cancer, organ rejection, graft versus host disease, autoimmunity, chronic infection, vaccine response, and the like.

In regard to cancer, methods of the invention may be used to identify antigens in tumors that TILs recognize. Such antigen identity may inform cancer vaccine design or selection of the best tumor reactive T cells for autologous cell therapy.

In regard to organ rejection, method of the invention may be used to improve tissue matching between donors and recipients. Even in HLA matched donors and recipients there is organ rejection and the necessity of recipient immunosuppression. Rejection is mediated by "minor antigens" presented by the graft. Minor antigens are essentially the T cell peptide epitopes that have amino acid sequence differences arising from SNPs in the donor genome that are different from the recipients SNPs. Methods of the invention may be used to identify the minor antigens that trigger recipient T cell responses. Likewise, in graft versus host disease, methods of the invention may be used to identify the minor antigens in a recipient that trigger donor T cell responses.

In regard to autoimmunity (e.g. multiple sclerosis, Crohn's disease, rheumatoid arthritis, type I diabetes, and the like), method of the invention may be used to identify underlying T cell antigens in the affected tissues which information, in turn, could be used to tolerize or deplete the reactive T cells causing the pathology.

Kits

The invention includes kits for carrying out the methods of the invention. In some embodiments, kits comprise mammalian reporter cells capable of expressing candidate epitope-encoding nucleic acids in the context of a membrane-bound major histocompatibility complex (MHC) protein and capable of expressing a signal-generating product responsive to an effector agent of a cytotoxic T-cell. Kits of the invention may further include vectors for transducing the mammalian reporter cells with an epitope-encoding library. Kits of the invention may further include vectors for transducing the mammalian reporter cells with a signaling system responsive to the presence of an effector agent, such as a granzyme, which signaling system may or may not be in the same vector as an epitope-encoding library. Kits of the invention may further include vectors for transducing the mammalian reporter cells with an MHC gene matched to an individual. Kits of the invention may further comprise instructions for (i) transducing the mammalian reporter cells with a vector including sequences encoding a signal generating product and (ii) transducing the mammalian reporter cells with a vector including candidate epitope-encoding nucleic acids. Kits of the invention may further include instructions for transducing the mammalian reporter cells with an MHC gene encoding MHC molecules matched to an individual. Kits of the invention may further comprise one or more vectors for transfecting and/or transducing the mammalian reporter cells so that such cells are capable of expressing candidate epitope-encoding nucleic acids to produce an MHC-epitope complex in the mammalian reporter cells. Kits of the invention may further comprise one or more vectors for transfecting and/or transducing the mammalian reporter cells so that such cells express a signal-generating product capable of generating a signal in response to contact with an effector agent. In some embodiments, such signal-generating product comprises a fluorescent protein and the effector agent is a granzyme B enzyme.

Example 1

Model Assays Based on Stably Transfected Mouse Lymphoblastic Cell Lines EL4 and EG7 as Model Reporter Cells In this example, CTLs were primary CD8+ splenocytes from OT-I transgenic mice which express an invariant TCR specific for the model ovalbumin (Ova) epitope SIINFEKL. The model APCs in this system are the mouse lymphoblast cell lines EL4 and a stably Ova-transfected derivative, EG7-Ova. To detect a cytotoxic hit to an APC by CTLs, the fluorogenic CellEvent™ Caspase-3/7 Green Detection Reagent from Invitrogen (Carlbad, Calif.) was used to detect the induction of apoptosis. Alternatively, a genetically-encoded CFP-YFP fusion FRET pair separated by a granzyme B (GzmB)-cleavable linker (FIGS. 2A-2B) may also be used. Experiments observing CTL attack on target APC using CellEvent™ Caspase 3/7 Detection Reagent have shown that induction of apoptosis is readily detectable by flow cytometry after as little as 1 hour. Further, persistence of signal is observed 24 hours (FIGS. 3A and 3B).

EL4 cells (Ova−) or EG7 cells (Ova+) were co-incubated with in vitro expanded CD8+ T-cells from the TCR transgenic mouse strain, OT-I, at a 5:1 effector:target ratio or with staurosporine (STS). Effector cells were stained with anti-Thy1.1 APC-eFluor780 and whole co-cultures were stained with CellEvent reagent. FIG. 3A shows co-cultures analyzed by flow cytometry. FIG. 3B shows 20× magnified images of cytotoxic attack on EG-7 (Ova+) cells by OT-1 CD8+ cells. The fluorescence image on top clearly shows readily distinguishable apoptotic cells. The corresponding bright-field image is displayed underneath.

Example 2

Confirming Function of Granzyme B-Sensitive Signal Generation Product

Testing of a granzyme B (GzmB)-sensitive signal generating product was carried out in an NK-92MI-HeLa system. NK-92MI is a human natural cell killer line which is capable of cytotoxicity via the GzmB pathway and the widely used cervical cancer line, HeLa, is a known target of these NK-92MI. The ease of transfection of HeLa cells and the non-epitope restricted cytotoxicity of NK-92MI provide an excellent platform for the assessment of GzmB-specific reporter systems. The data in FIG. 4 show a decrease of FRET signal and a concomitant increase in CFP signal resulting in a when NK-92MI are cultured with CFP-YFP HeLa transfectants. The resulting diagonal shift in FRET vs. CFP plots is large enough to enable gating of putative positive targets from negatives.

Example 3

Model Assays Based on Stably Transfected Mouse Ovarian Cell Lines ID8 and ID8.G7-Ova as Reporter Cells In this example, experiments were carried out to test the ability of the sort-and-sequence method to enrich for a population of cells containing the appropriate target antigen sequence. FIG. 5A shows the experimental workflow and results from the experiment. CTLs were primary CD8+ splenocytes from OT-I transgenic mice which express an invariant TCR specific for the model ovalbumin (Ova) epitope SIINFEKL. There are no immortalized CD8+ T-cell lines available that retain cytolytic function. Therefore, for initial development, a CTL system comprising replenishable primary CD8+ splenocytes from OT-I transgenic mice was used. These CD8+ T-cells express an invariant TCR specific for the model chicken ovalbumin antigen SIINFEKL, which is irrelevant biologically but is a high-affinity binder to the mouse MHC class I molecule H-2Kb. The model reporter cells in this system are the mouse ovarian tumor cell lines ID8 and a stably Ova-transfected derivative, ID8.G7-Ova. ID8 expresses the H-2Kb-coded MHC I isoform.

Returning to FIG. 5A, mixture of cells transiently transfected with either the Ova minigene (500) or the Ova-scrambled minigenes (502) was made at a known ratio. After culture with or without CTLs (504), minigenes contained in FACS recovered cells (508 for CTL− and 510 for CTL+) were amplified (512) using flanking primers. Amplicons were cloned and 96 colonies from each of the background gate of the CTL− cultures and the targeted gate of the CTL+ cultures were sequenced (514). The results (bars 516 and 518) indicate that, while there was some specific isolation of the correct epitope, there was a high level of background, which was determined to be likely due to contamination with NK cells that killed target cells nonspecifically.

Minigenes were synthesized that coded for either the targeted SIINFEKL epitope (minOva) or a codon-scrambled negative control epitope (minOScr) plus, in each case, 16 flanking residues on either side of the epitope. A lentiviral vector system (diagrammatically illustrated in FIG. 2C) was constructed with the FRET reporter encoded downstream of the minigene separated by coding sequence for a member of the self-cleaving 2A peptide family. Expression is under the control of the strong MND promoter.

Example 4

Model Assays Based on Lentivirus-Transduced Mouse Ovarian Cell Lines ID8 and ID8.G7-Ova as Reporter Cells In this example, ID8 cells were transduced using a lentivirus vector with each of the Ova minigenes and the experiment outlined in FIG. 5A was repeated with these cell lines. That is, target ID8 lentivirally transduced with either OVA minigene (minOva) or OVA minigene containing scrambled epitope (minOScr) were cultured with or without OT-I CD8+ T-cells at a 1:1 ratio for 4 hrs. The results indicate much more uniform signal in the positive and negative FRET gates and, notably, the loss of the large "plume" of cells seen at the lower intensity ranges of FIG. 5A (508 and 509). The stability and efficiency of this method enables for the enrichment and outgrowth of positively transduced, highly-expressing target cells to yield higher-quality signal for screening experiments. The relatively low copy numbers of vector DNA introduced to the host nucleus compared to chemical or electrical methods of transfection ensures that, in the case of antigen libraries, background from false positive sequences sorted along with true positives will be minimized. Results of this example are illustrated in FIGS. 5B and 5C and are summarized in the figure captions above.

Example 5

Assay Based on Autologous B-Lymphoblastoid Cell Line (B-LCL) as Reporter Cells

In this example, CTLs are from a patient derived CD8+ T-cell clone which has known reactivity to the human Melan-A/MART-1(26-35)-Leu27 epitope, ELAGIGILTV. As antigen-presenting cells (i.e. reporter cells), an autologous B-lymphoblastoid cell line (B-LCL) has been developed by EBV transformation of cells originating from the same patient as the MART-1 specific T-cell clone. B-LCL cells are cultured with or without CTLs at a 1:1 ratio for 4 hrs. Data show specific targeting by CTLs based on the percentage of B-LCL cells generating a FRET signal.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immuology, $6^{th}$ edition (Saunders, 2007).

"Antigen presenting cell" or "APC" means a cell that displays peptide fragments of protein antigens, in association with MHC molecules, on its surface, and activates antigen-specific T cells. For example, cytotoxic T cells are activated to generate an effector response.

"Apoptosis" means a process of cell death characterized by DNA cleavage, nuclear condensation and fragmentation, and plasma membrane blebbing that leads to phagocytosis of the cell without inducing an inflammatory response.

"Cytotoxic T-cell" or "cytotoxic T-lymphocyte" ("CTL") means a type of T cell that secrets effector agents on recognition of a target cell by the specific binding its T cell receptor to an MHC molecule on the target cell complexed with an epitope. CTLs are characterized by the presence of the CD8 cell surface receptor.

"Epitope" or "target antigen of a cytotoxic lymphocyte" means any molecule that may be presented to a cytotoxic lymphocyte in an MHC-restricted format. Usually, an epitope is a portion of a protein, i.e. a peptide, which binds to, or is complexed with, an MHC molecule for recognition by a cytotoxic lymphocyte. Such peptide epitopes may include posttranslational modifications, such as carbohydrate or lipid moieties.

"Effector agent" means a constituent of a lytic granule. Lytic granules are described in Clark et al, Curr. Opin. Immunol., 15(3): 516-521 (2003); Page et al, Biochim. Biophys. Acta, 1401(2): 146-156 (1998), which are incorporated herein by reference. In some embodiments, an effector agent is a compound secreted released by a cytotoxic lymphocyte by exocytosis of a granule. In some embodiments, such exocytosis results from the upon specific binding of its cytotoxic lymphocyte receptors to MHC-epitope complexes on the surface of a target cell. In other embodiments, such exocytosis results from the specific binding of chimeric antigen receptors (CARs) of a cytotoxic lymphocyte to CAR-specific molecules of a target cell, for example, cognate surface antigens of a target cell. An In some embodiments, an effector agent, either alone or with other molecules, is capable of directly or indirectly triggering an apoptotic pathway of the target cell. In some embodiments, the term "effector agent" refers to protein effector agents, such as a granzyme. Effector agents include, but are not limited to, granzymes, perforins, and granulysins.

"Effector response" or "effector function" in reference to a cytotoxic lymphocytes means activation after recognition of an MHC-epitope of a target call of a lytic granule killing mechanism that includes formation of intracellular granules, loading of granules with effector agents, and transport and exocytosis of effector agents in the vicinity of the target cell, e.g. as described by Cullen et al, Cell Death and Differentiation, 15: 251-262 (2008); Trapani et al, Nature Reviews Immunology, 2: 735-747 (2002).

"Granzyme" or "granzyme protein" means a serine protease found in the granules of cytotoxic lymphocytes, such as CTLs and natural killer (NK) cells, that is released by exocytosis, enters target cells, mainly through perforin-created membrane pores, and proteolytically cleaves and activates caspases, which in turn cleave several substrates and induce target cell apoptosis. In some embodiments, a granzyme is a human granzyme. In other embodiments, a human granzyme includes granzymes A, B, H, K or M, separately or together. In other embodiments, a granzyme is a human granzyme B. Granzymes and their functions are described in Cullen et al, Cell Death and Differentiation, 15: 251-262 (2008); Symthe et al, J. Leukocyte Biol., 70: 18-29 (2001); and like references "Granzyme-perforin pathway" means a process for delivering effector agents in lytic granules of a first cell, usually a cytotoxic lymphocyte, to the cytosol of a second cell, i.e. a target cell. Elements of the process include transportation of lytic granules in the cytosol of the first cell to its cell membrane and exocytosis of the lytic granule contents into the intercellular space adjacent to the target cell. Other elements of the process involve the functions of the contents of the lytic granules. In humans there are four granzymes: A, B, K and M, of which granzyme B (GzB) is the best characterized, most abundant (along with granzyme A), and the focus of this proposal. GzB is a serine protease with a classical trypsin-like catalytic triad that initiates apoptosis in targeted cells. Synthesized primarily in cytotoxic lymphocytes as a 247 amino acid precursor protein, GzB is directed to the endoplasmic reticulum by a signal peptide, which is subsequently cleaved, yielding the zymogen form of GzB, which is still inactive due to a N-terminal dipeptide. This proenzyme is sorted through the Golgi network in a pathway that involves the addition of mannose-6-phosphate, as well as the chaperone molecule serglycin, both of which promote localization of GzB to lytic granules (LGs), a type of specialized secretory lysososome. Here the dipeptide is cleaved by cathepsin C, and the active form of GzB is safely sequestered in the acidic LG and stored there awaiting CTL activation. The other major component of this pathway is perforin, a long, thin protein that forms pores in targeted cells, and is stored in LGs along with granzyme-serglycin aggregates. Upon TCR engagement in an activated CTL, a tight enclosed region between the CTL and target cell forms, which is known as the immunological synapse (IS). Perforin and granzyme are exocytosed from the LGs into the IS, and diffuse across to the target cell membrane, into which perforin inserts, and then aggregates to form multimeric, transmembrane pores. Historically it was thought that these perforin pores were directly responsible for target cell death, but it is now believed that physiological concentrations of perforin alone are not cytotoxic. Instead, the pores seem to be only briefly patent before membrane integrity is restored, with their main function being a conduit for passive diffusion of effector agents, such as granzyme B, into the target cell. Once in the cytosol, it is the effector agents, such as, GzB for example that initiates apoptosis by cleavage of BH3 interacting-domain death agonist (BID) and caspases 3, 7 and 8, which in turn activate the mitochondrial and caspase apoptosis pathways respectively.

"Kit" means any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Major histocompatibility complex" ("MHC") molecule means a heterodimeric membrane protein encoded in the MHC locus that serves as a peptide display molecule for recognition by T lymphocytes. For MHC molecules of different samples of cells or tissue to be "matched" means that cells of the different samples express the same genetic variant of an MHC molecule.

"Perforin" means a cellular membrane pore forming protein produced by cytotoxic lymphocytes upon stimulation of a cell death pathway, e.g. Trapani et al, Nature Reviews Immunology, 2: 735-747 (2002); Keefe et al, Immunity, 23: 249-262 (2005); Catalfamo et al, Curr. Opin. Immunol., 15: 522-527 (2003).

"Peptide" or "polypeptide" refers to a class of compounds composed of amino acid residues chemically bonded together by amide linkages with elimination of water between the carboxy group of one amino acid and the amino group of another amino acid. In some embodiments, peptides comprise a linear chain of amino acids having a length in the range of from 6 to 20 amino acids. In other embodiments, peptides comprise a linear chain of amino acids having a length in the range of from 8 to 14 amino acids.

"Polymerase chain reaction" or "PCR" means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. Reaction volumes typically range from a few hundred nanoliters, e.g. 200 nL, to a few hundred µL, e.g. 200 µL. "Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Transgene" means natural or artificially constructed genetic material that has been transferred naturally, or by any of a number of genetic engineering techniques, to an organism or from one organism to another.

"Transfection" and/or "transformation" and/or "transduction" are used synonymously herein mean transfer of exogenous genetic material to a target mammalian cell. Such transfer may result in temporary or transient expression of a transgene or temporary or transient transcription of an RNA in a target mammalian cell, for example, because of exhaustion of genetic material, loss or degradation of genetic material, lack of replication of genetic material, or the like. In some embodiments, "transfection" means "stable transfection" as the latter term is commonly used, e.g. Kim et al, Anal. Bioanal. Chem., 379: 3173-3178 (2010). Exogenous genetic material may include plasmids, viral vectors, transgenes, transposons, or the like. "Stable" as used herein means that the exogenous genetic material persists through multiple cell divisions or for the life, or substantially for the life, of the cellular host. The exogenous genetic material may be integrated into the genome of a target mammalian cell or it may comprise episomal DNA, such as a plasmid. Typically, stably transferred genetic material expresses one or more proteins of interest in a target mammalian cell.

"Vector" means a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

What is claimed is:

1. A method for determining epitopes recognized by cytotoxic T-cells, the method comprising the steps of:
    expressing a library of candidate epitope-encoding nucleic acids in reporter cells capable of presenting expressed peptides of such candidate epitope-encoding nucleic acids in the context of a membrane-bound major histocompatibility complex (MHC) protein wherein the reporter cells are modified to carry a fluorescence-based signaling system in their cytosols that generates a fluorescent signal whenever a peptide linkage in the system is enzymatically cleaved by a granzyme A, B, H, K or M from granules of a cytotoxic T cell upon recognition of an expressed peptide in the context of an MHC protein on a reporter cell by such cytotoxic T cell;
    contacting in a reaction mixture a mixed population of the reporter cells expressing different candidate epitope-encoding nucleic acids of the library with a sample comprising cytotoxic T-cells, wherein effector functions of cytotoxic I-cells recognizing reporter cells are activated so that granzyme A, H, K or M in granules of the Cytotoxic T-cells are delivered by, a granzyme-perforin pathway to recognized reporter cells and cause a fluorescent signal to be venerated by the reporter cells;
    isolating intact reporter cells generating fluorescent signals;
    extracting candidate epitope-encoding nucleic acids from the isolated intact reporter cells; and
    sequencing the candidate epitope-encoding nucleic acids of the reporter cells to identify the epitope-encoding nucleic acids.

2. The method of claim 1 wherein said sample is from an individual and said MHC proteins of said reporter cells are matched with MHC proteins expressed by the individual.

3. The method of claim 2 wherein said reporter cells comprise autologous cells of said individual genetically modified to express candidate epitopes of said library.

4. The method of claim 3 wherein said autologous cells are B cells of said individual.

5. The method of claim 4 wherein said autologous cells are stably transfected or transformed by a vector capable of expressing said candidate epitopes of said library.

6. The method of claim 3 wherein said reporter cells are genetically modified to express a FRET-based fluorescent protein signaling system that generates a fluorescent signal whenever enzymatically cleaved by one of said granzyme A, B, H, K or M.

7. A method for determining epitopes recognized by cytotoxic T-cells, the method comprising the steps of:
    (a) expressing a library of candidate epitope-encoding nucleic acids or an enriched library of candidate epitope-encoding nucleic acids in reporter cells capable of presenting expressed peptides of such candidate epitope-encoding nucleic acids in the context of a membrane-bound major histocompatibility complex (MHC) protein wherein the reporter cells are modified to carry a fluorescence-based signaling system that generates a fluorescent signal whenever a peptide linkage in the system is enzymatically cleaved by a granzyme A, B, H, K or M from granules of a granzyme-perforin pathway of a cytotoxic T cell upon recognition of an expressed peptide in the context of an MHC protein on a reporter cell by such cytotoxic T cell;

(b) contacting in a reaction mixture a mixed population of the reporter cells expressing different candidate epitope-encoding nucleic acids of the library with a sample comprising cytotoxic T-cells;

(c) isolating reporter cells generating a fluorescent signal indicating recognition by a cytotoxic T-cell;

(d) extracting candidate epitope-encoding nucleic acids from the isolated reporter cells and generating therefrom an enriched library of candidate epitope-encoding nucleic acids;

(e) repeating steps (a)-(d) with the enriched library of candidate epitope-encoding nucleic acids until a frequency of reporter cells generating the signal indicating recognition by a cytotoxic T-cell is greater than or equal to a predetermined value;

(f) sequencing the candidate epitope-encoding nucleic acids of reporter cells generating said signal to identify sequences of the epitope-encoding nucleic acids.

8. The method of claim 7 wherein said step of isolating includes sorting said reporter cells by a fluorescently activated cell sorter (FACS).

* * * * *